US00PP35211P2

(12) United States Plant Patent
Gielis

(10) Patent No.: US PP35,211 P2
(45) Date of Patent: Jun. 6, 2023

(54) ***SEMPERVIVUM* PLANT NAMED 'BELSEMYEL2'**

(50) Latin Name: *Sempervivum arachnoideum*
Varietal Denomination: Belsemyel2

(71) Applicant: Belgicactus B.V.B.A., Westerlo (BE)

(72) Inventor: Jef Gielis, Westerlo (BE)

(73) Assignee: BELGICACTUS B.V.B.A., Westerlo (BE)

( * ) Notice: Subject to any disclaimer, the term of this patent is extended or adjusted under 35 U.S.C. 154(b) by 0 days.

(21) Appl. No.: 18/082,085

(22) Filed: Dec. 15, 2022

(51) Int. Cl.
*A01H 5/02* (2018.01)
*A01H 6/32* (2018.01)

(52) U.S. Cl.
USPC ..... Plt./263.1
CPC ..... *A01H 6/32* (2018.05)

(58) Field of Classification Search
USPC ..... Plt./263.1, 373
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Sempervivum* plant named 'Belsemyel2' characterized by its compact plant habit, its growth habit that produces many offset rosettes, its strong root system, its good suitability for outdoor growing the entire year, its leaf surfaces that are covered with small white cobweb pubescence, and its range of foliage colors that are red-yellow in early spring, yellow with red centers in late spring, bright yellow in the summer, and yellow-green in autumn and winter.

2 Drawing Sheets

Botanical classification: *Sempervivum arachnoideum.*
Variety denomination: 'Belsemyel2'.

CROSS REFERENCE TO A RELATED APPLICATION

This application is related to a European plant breeders' rights application filed on Nov. 27, 2020, application No. 2020/3042 and a plant breeders' rights application in the United Kingdom on Jun. 7, 2022, application No. 23/774. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Sempervivum arachnoideum* plant and referred to hereinafter by its cultivar name, 'Belsemyel2'. The new cultivar of *Sempervivum* is a hardy succulent perennial grown for use as a landscape and container plant.

The new cultivar resulted from a controlled breeding program conducted by the Inventor in Westerlo, Belgium. The Inventor made a cross in 2013 between unnamed and unpatented plants of *Sempervivum arachnoideum* in the Inventor's breeding program as both the female and male parents. 'Belsemyel2' was selected as a single unique plant in July of 2015 from the resulting seedlings of the above cross.

Asexual propagation of the new cultivar was first accomplished by the Inventor by cuttings in 2015 in Westerlo, Belgium. Asexual propagation by cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'Belsemyel2' as a unique cultivar of *Sempervivum.*

1. 'Belsemyel2' exhibits a compact plant habit.
2. 'Belsemyel2' exhibits a growth habit that produces many offset rosettes.
3. 'Belsemyel2' exhibits a strong root system.
4. 'Belsemyel2' exhibits good suitability for outdoor growing the entire year.
5. 'Belsemyel2' exhibits leaf surfaces that are covered with small white cobweb pubescence.
6. 'Belsemyel2' exhibits a range of foliage colors that are red-yellow in early spring, yellow with red centers in late spring, bright yellow in the summer, and yellow-green in autumn and winter.

The female parent of 'Belsemyel2' differs from 'Belsemyel2' in having reddish brown foliage in spring and green foliage in summer and autumn. The male parent of 'Belsemyel2' differs from 'Belsemyel2' in having foliage that stays green in color. 'Belsemyel2' can be most closely compared to the *Sempervivum* cultivars 'Jubilee' (not patented), 'Kramer Spinrad' (not patented), and 'Solar Kugel' (not patented). 'Jubilee' is similar to 'Belsemyel2' in having green and red foliage coloration. 'Jubilee' differs from 'Belsemyel2' in having rosettes that are smaller in size, foliage that does not become yellow in color, and in having more densely covered cobweb pubescence. 'Kramer Spinrad' is similar to 'Belsemyel2' in growth habit and rosette size. 'Kramer Spinrad' differs from 'Belsemyel2' in being more densely covered with cobweb pubescence and in becoming and staying green in color as it matures. 'Solar Kugel' differs from 'Belsemyel2' in being more densely covered with cobweb pubescence and in having leaves that are longer and all green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listing by Plantipp, Facebook and Instagram (Colorockz), Globe Planter, Assets Publishing Service, and Pepinieres.

BRIEF DESCRIPTION OF THE DRAWINGS

The accompanying color photographs illustrate the overall appearance and distinct characteristics of 1.5-year-old plants of the new *Sempervivum* as grown outdoors in 8.5-cm containers in Westerlo, Belgium.

The photograph in FIG. 1 provides a view of the transitioning foliage color in spring and the cobweb pubescence of 'Belsemyel2'.

Figure 1:
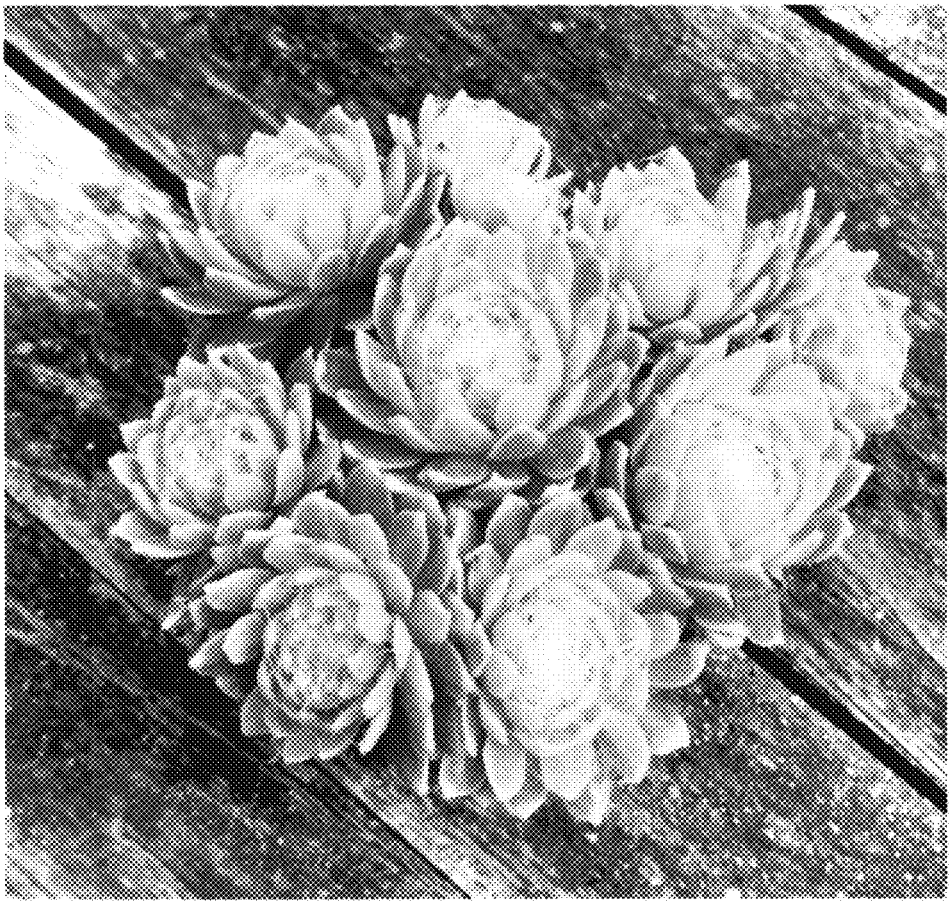
Figure 2:
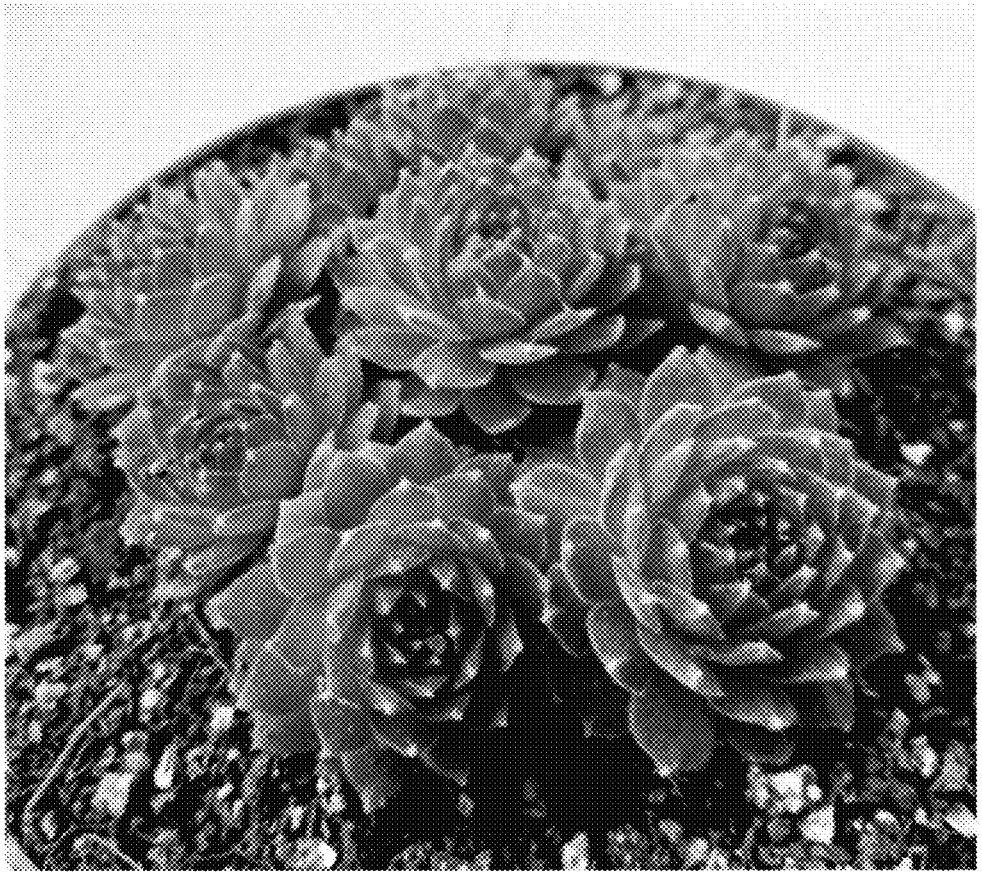

The photograph in FIG. 2 provides a view of the winter foliage of 'Belsemyel2'.

The colors in the photographs may differ slightly from the color values cited in the detailed botanical description, which accurately describe the colors of the new *Sempervivum*.

DETAILED BOTANICAL DESCRIPTION

The following is a detailed description of the new cultivar as observed on 1.5-year-old plants of the new *Sempervivum* as grown outdoors in 8.5-cm containers in Westerlo, Belgium. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen succulent perennial.

*Plant habit*.—Basal rosette, offsets clustered around main rosette.

*Height and spread*.—Reaches up to 4 cm in height and 13 cm in spread (with off shoots), average diameter of main rosette is 6 cm.

*Hardiness*.—At least in U.S.D.A. Zones 3 to 9.

*Diseases and pests*.—No susceptibility or resistance to diseases or pests has been observed; (*Sempervivums* are generally disease free unless grown under wet and cold conditions).

*Root description*.—Rhizomes grow from main rosette and hold offsets, rounded in shape, average of 2.5 cm in length and 1.5 mm in width, texture smooth, glabrous and matte, 200D in color.

*Propagation*.—Cuttings.

*Root development*.—A cutting taken in July will fully root in September/October and will fill a P9 container in June.

*Growth rate*.—Rapidly produces offset rosettes.

Stem description: Stemless.

Foliage description:

*Leaf shape*.—Oblong, succulent.

*Leaf division*.—Simple.

*Leaf arrangement*.—Rosette.

*Leaf base*.—Broad cuneate.

*Leaf apex*.—Abruptly apiculate.

*Leaf venation*.—No veins visible.

*Leaf margins*.—Ciliate and unlobed.

*Leaf attachment*.—Sessile.

*Leaf orientation*.—Slightly curved upward.

*Leaf substance*.—Succulent, average of 2 mm in thickness.

*Leaf number*.—An average of 70 per rosette.

*Leaf surface*.—Both surfaces are glaucescent, smooth, covered with short glandular hairs, tips and middle of the rosette are lightly covered with thin cobweb type hairs, NN155A in color.

*Leaf color*.—Fall and winter; upper and lower surface 145A and 145B, Spring; upper and lower surface center leaves 145A, upper and lower surface outer leaves of rosette N34A and 20B.

*Leaf size*.—Average of 2 cm in length and 8 mm in width.

Flower description: No flowers have been observed to date under numerous growing situations.

It is claimed:

1. A new and distinct variety of *Sempervivum* plant named 'Belsemyel2' as described and illustrated herein.

* * * * *